US012778422B2

(12) United States Patent
Steele et al.

(10) Patent No.: US 12,778,422 B2
(45) Date of Patent: Nov. 3, 2026

(54) RISK-ADAPTIVE TELEMETRY AND REMOTE MONITORING

(71) Applicant: Dexcom, Inc., San Diego, CA (US)

(72) Inventors: Colin Anthony Steele, San Diego, CA (US); Stephen D. Patek, Charlottesville, VA (US)

(73) Assignee: Dexcom, Inc., San Diego, CA (US)

( * ) Notice: Subject to any disclaimer, the term of this patent is extended or adjusted under 35 U.S.C. 154(b) by 331 days.

(21) Appl. No.: 18/434,955

(22) Filed: Feb. 7, 2024

(65) Prior Publication Data

US 2024/0268669 A1 Aug. 15, 2024

Related U.S. Application Data

(60) Provisional application No. 63/444,699, filed on Feb. 10, 2023.

(51) Int. Cl.

| | |
|---|---|
| ***A61B 5/00*** | (2006.01) |
| ***A61B 5/145*** | (2006.01) |
| ***G16H 40/67*** | (2018.01) |

(52) U.S. Cl.

CPC ........ *A61B 5/0022* (2013.01); *A61B 5/14532* (2013.01); *A61B 5/486* (2013.01); *A61B 5/7275* (2013.01); *G16H 40/67* (2018.01)

(58) Field of Classification Search

CPC ... A61B 5/0022; A61B 5/14532; A61B 5/486; A61B 5/7275; A61B 2560/0276; G16H 40/67; G16H 40/63; G16H 50/30

See application file for complete search history.

(56) References Cited

U.S. PATENT DOCUMENTS

| | | | | |
|---|---|---|---|---|
| 11,868,479 | B2 * | 1/2024 | Lysecky | G06F 21/566 |
| 12,109,033 | B1 * | 10/2024 | Duffy | A61B 5/282 |
| 2002/0181680 | A1 * | 12/2002 | Linder | A61N 1/37247 379/106.02 |
| 2018/0083884 | A1 | 3/2018 | Kuang | |
| 2019/0365301 | A1 | 12/2019 | Rasmusson et al. | |
| 2022/0211332 | A1 * | 7/2022 | Demmer | A61B 5/076 |
| 2022/0379029 | A1 * | 12/2022 | Zade | A61M 5/1723 |
| 2023/0346231 | A1 * | 11/2023 | Mcgrath | A61B 5/02416 |

OTHER PUBLICATIONS

Sarma J., et al., "VLSI based Adaptive Power Management Architecture for ECG Monitoring in WBAN," 2020 33rd International Conference on VLSI Design and 2020 19th International Conference on Embedded Systems (VLSID), Jan. 4, 2020, pp. 113-118.

* cited by examiner

*Primary Examiner* — Stella L. Woo

(74) *Attorney, Agent, or Firm* — Klarquist Sparkman, LLP

(57) ABSTRACT

In accordance with a method of communicating telemetry data employed by a risk-adaptive telemetry system, a medical device risk that a medical device will malfunction is assessed. A patient risk that the health of a patient using the medical device will fall below a predetermined acceptable level is also assessed. Telemetry data from the medical device is received, where type, amount and/or frequency of the telemetry data that is received is based at least in part on the assessed medical device risk and the patient risk.

53 Claims, 4 Drawing Sheets

RISK-ADAPTIVE TELEMETRY AND REMOTE MONITORING

CROSS-REFERENCE TO RELATED APPLICATION

This application claims the benefit of U.S. Provisional Application Ser. No. 63/444,699, filed Feb. 10, 2023, the contents of which are incorporated herein by reference.

BACKGROUND

Various types of medical devices are used to administer and deliver a therapy to a patient and/or monitor a condition of the patient. Illustrative examples of such medical devices may include wearable, embedded, implantable and remote devices including, without limitation, heart monitors, physiological sensors and monitors such as blood glucose monitors, pacemakers, implantable defibrillators, medicant delivery devices (e.g., insulin pumps and pens), neurostimulation devices, and so on.

The aforementioned medical devices generally are used by patients on an ongoing basis outside of a health care facility (e.g., a hospital, clinic, a physician or other health care provider's office) and perform their treatment and/or monitoring functions without being under the direct operational control of a health care provider. Accordingly, such medical devices are often interrogated to collect operational and/or physiological data stored in the medical device, or to monitor the current condition of the device or the patient. In each case, a telemetry session is established with the medical device to obtain the data.

Telemetry sessions between the medical device and a remote telemetry station may be conducted over any suitable communications network or combination of networks (e.g., wired and/or wireless). The growing ubiquity of network connectivity points in principle allow a nearly unlimited resolution to be achieved in the ability to capture and understand the state of a remote system such as a medical device. However, engineering trade-offs remain, including those involving power, volatile and nonvolatile storage, computer cycles, and so on, which are required for storage, transmission and ingestion, etc. For instance, medical devices typically operate by battery power. The batteries may or may not be rechargeable. Regardless, however, it is desirable to lower the power consumption of the device. Higher consumption of power from a medical device containing rechargeable batteries leads to more frequent charging periods for the batteries and associated inconvenience and, in the case of implantable medical devices, may lead to an increased frequency of surgery, potential pain, recovery and inconvenience. As telemetry reception and transmission are highly energy consumptive, it is desirable to minimize the operation time of telemetry reception and transmission modules. The promise and ability to achieve near infinite telemetry resolution thus comes at a similarly near infinite cost.

SUMMARY

Systems and methods are described herein for reducing the resolution (and cost) of remote telemetry and monitoring while simultaneously improving its performance and utility. In the circumstances where telemetry is obtained from not only the medical device but also the person using the medical device, a unique opportunity exists to drive the resolution (and hence cost) of "infinite monitoring" down while also improving the utility of telemetry. When risk to the person is low and well known, the value of telemetry is diminished. Conversely, when risk to the person is high, or unknown, the value of telemetry rises. Tying strategies for telemetry and remote monitoring to risk (in particular, health or safety risk) represents a significant opportunity to optimize the telemetry process.

In a first aspect, a method of determining telemetry data that is to be transmitted to a remote location is presented. The method includes: receiving patient data describing a state of a patient who uses a medical device; receiving medical device data describing a state of the medical device; assessing patient risk based at least in part on the patient data that is received, the patient risk reflecting (i) a likelihood that the patient has entered or will enter a patient risk state representative of one or more predetermined physical conditions that do not meet a prescribed level of patient health and (ii) a severity level of the patient risk state; assessing medical device risk based at least in part on the medical device data that is received, the medical device risk reflecting (i) a likelihood that the medical device has entered or will enter a medical device risk state indicating that operability of the medical device does not meet a prescribed standard and (ii) a severity level of the device risk state; and selecting for transmission to a remote location selected telemetry data associated with the medical device and/or the patient in a manner that is based at least in part on the assessed medical device risk and the assessed patient risk.

In an embodiment of the first aspect, the method further includes receiving environmental data describing a state of an environment in which the medical device and/or the patient is located, wherein assessing the medical device risk and the patient risk is further based at least in part on the environmental data.

In an embodiment of the first aspect, the method further includes causing an adjustment to an amount, type and/or frequency of receipt of the medical device data that is received based at least in part on the assessed medical device risk and the assessed patient risk.

In an embodiment of the first aspect, the method further includes causing an adjustment to an amount, type and/or frequency of receipt of the patient data that is received based at least in part on the assessed medical device risk and the assessed patient risk.

In an embodiment of the first aspect, the method further includes causing an adjustment to the amount, type and/or frequency of receipt of the patient data that is received based at least in part on the assessed medical device risk and the assessed patient risk.

In an embodiment of the first aspect, the method of claim 1, wherein selecting for transmission selected telemetry data in a manner that is based at least in part on the assessed medical device risk and the assessed patient risk includes determining a type of telemetry data that is to be transmitted to the remote location and/or a frequency at which the telemetry data is to be transmitted to the remote location.

In an embodiment of the first aspect, the types of telemetry data that are selected and/or the frequency at which the telemetry data is selected for transmission increases as the assessed medical device risk and/or the assessed patient risk increases.

In an embodiment of the first aspect, the types of telemetry data that are selected and/or the frequency at which the telemetry data is selected for transmission decreases as the assessed medical device risk and/or the assessed patient risk decreases.

In an embodiment of the first aspect, the medical device is a continuous glucose monitor and the patient data includes blood glucose data.

In an embodiment of the first aspect, the medical device is selected from the group including pacemakers, implantable defibrillators, medicant delivery devices and neurostimulation devices.

In an embodiment of the first aspect, the method further includes locally storing telemetry data that is not selected for transmission.

In an embodiment of the first aspect, the method further includes selecting for transmission to the remote location at least some of the locally stored telemetry data when the assessed medical device risk and/or the assessed patient risk increases.

In an embodiment of the first aspect, different types of medical device data are obtained using different types of sensors.

In an embodiment of the first aspect, at least one of the sensors is embedded with the medical device.

In an embodiment of the first aspect, at least one of the sensors is external to the medical device.

In an embodiment of the first aspect, the patient risk and/or the medical device risk is determined using a state calculation that accounts for previous risk states.

In an embodiment of the first aspect, the patient data is received at least in part from the medical device.

In a second aspect, a risk-adaptive telemetry system is presented. The system includes a processor configured to: receive patient data from a medical device describing a state of a patient; receive medical device data describing a state of the medical device; assess patient risk based at least in part on the patient data that is received, the patient risk reflecting (i) a likelihood that the patient has entered or will enter a patient risk state representative of one or more predetermined physical conditions that do not meet a prescribed level of patient health and (ii) a severity level of the patient risk state; assess medical device risk based at least in part on the medical device data that is received, the medical device risk reflecting (i) a likelihood that the medical device has entered or will enter a device risk state indicating that operability of the medical device does not meet a prescribed standard and (ii) a severity level of the device risk state; and select for transmission to a remote location telemetry data associated with the medical device and/or the patient in a manner that is based at least in part on the assessed medical device risk and the assessed patient risk.

In an embodiment of the second aspect, the processor is further configured to receive environmental data describing a state of an environment in which the medical device and/or the patient is located, wherein assessing the medical device risk and the patient risk is further based at least in part on the environmental data.

In an embodiment of the second aspect, the processor is further configured to cause an adjustment to an amount, type and/or frequency of receipt of the medical device data that is received based at least in part on the assessed medical device risk and the assessed patient risk.

In an embodiment of the second aspect, the processor is further configured to cause an adjustment to an amount, type and/or frequency of receipt of the patient data that is received based at least in part on the assessed medical device risk and the assessed patient risk.

In an embodiment of the second aspect, the processor is further configured to cause an adjustment to the amount, type and/or frequency of receipt of the patient data that is received based at least in part on the assessed medical device risk and the assessed patient risk.

In an embodiment of the second aspect, selecting for transmission selected telemetry data in a manner that is based at least in part on the assessed medical device risk and the assessed patient risk includes determining a type of telemetry data that is to be transmitted to the remote location and/or a frequency at which the telemetry data is to be transmitted to the remote location.

In an embodiment of the second aspect, the types of telemetry data that are selected and/or the frequency at which the telemetry data is selected for transmission increases as the assessed medical device risk and/or the assessed patient risk increases.

In an embodiment of the second aspect, the types of telemetry data that are selected and/or the frequency at which the telemetry data is selected for transmission decreases as the assessed medical device risk and/or the assessed patient risk decreases.

In an embodiment of the second aspect, the medical device is a continuous glucose monitor and the patient data includes blood glucose data.

In an embodiment of the second aspect, the medical device is selected from the group including pacemakers, implantable defibrillators, medicant delivery devices and neurostimulation devices.

In an embodiment of the second aspect, the processor is further configured to locally store telemetry data that is not selected for transmission.

In an embodiment of the second aspect, the processor is further configured to select for transmission to the remote location at least some of the locally stored telemetry data when the assessed medical device risk and/or the assessed patient risk increases.

In an embodiment of the second aspect, different types of medical device data are obtained using different types of sensors.

In an embodiment of the second aspect, at least one of the sensors is embedded with the medical device.

In an embodiment of the second aspect at least one of the sensors is external to the medical device.

In an embodiment of the second aspect, the patient risk and/or the medical device risk is determined using a state calculation that accounts for previous risk states.

In an embodiment of the second aspect, the patient data is received at least in part from the medical device.

In a third aspect, a method is presented of communicating telemetry data. The method includes: assessing a medical device risk that a medical device will malfunction; assessing a patient risk that health of a patient using the medical device will fall below a predetermined acceptable level; and receiving telemetry data from the medical device, wherein a type, amount and/or frequency of the telemetry data that is received is based at least in part on the assessed medical device risk and the patient risk.

In an embodiment of the third aspect, the patient risk state is determined at least in part on data received from the medical device.

In an embodiment of the third aspect, the method further includes assessing an additional risk state of at least one computing device employed in the assessing and/or receiving and wherein receiving telemetry data from the medical device includes receiving an amount and/or frequency of the telemetry data based at least in part on the assessed additional risk state.

In an embodiment of the third aspect, the method further includes receiving environmental data describing a state of an environment in which the medical device and/or the patient is located, wherein assessing the medical device risk and the patient risk is further based at least in part on the environmental data.

In an embodiment of the third aspect, the method further includes receiving medical device data describing a state of the medical device and causing an adjustment to an amount, type and/or frequency of the medical device data that is received based at least in part on the assessed medical device risk and/or the assessed patient risk.

In an embodiment of the third aspect, the method further includes receiving patient data describing a state of the patent and causing an adjustment to an amount, type and/or frequency of the patient data that is received based at least in part on the assessed medical device risk and/or the assessed patient risk.

In an embodiment of the third aspect, the method further includes causing an adjustment to the amount, type and/or frequency of receipt of the patient data that is received based at least in part on the assessed medical device risk and/or the assessed patient risk.

In an embodiment of the third aspect, the types of telemetry data that are selected and/or the frequency at which the telemetry data is selected for transmission increases as the assessed medical device risk and/or the assessed patient risk increases.

In an embodiment of the third aspect, the types of telemetry data that are selected and/or the frequency at which the telemetry data is selected for transmission decreases as the assessed medical device risk and/or the assessed patient risk decreases.

In an embodiment of the third aspect, the medical device is a continuous glucose monitor and the patient data includes blood glucose data.

In an embodiment of the third aspect, the medical device is selected from the group including pacemakers, implantable defibrillators, medicant delivery devices and neurostimulation devices.

In an embodiment of the third aspect, the method further includes selecting for transmission to a remote location at least a portion of the telemetry data that is received and locally storing telemetry data that is not selected for transmission.

In an embodiment of the third aspect, the method further includes selecting for transmission to the remote location at least some of the locally stored telemetry data when the assessed medical device risk and/or the assessed patient risk increases.

In an embodiment of the third aspect, different types of medical device data are obtained using different types of sensors.

In an embodiment of the third aspect, at least one of the sensors is embedded with the medical device.

In an embodiment of the third aspect, at least one of the sensors is external to the medical device.

In an embodiment of the third aspect, the patient risk and/or the medical device risk is determined using a state calculation that accounts for previous risk states.

In an embodiment of the third aspect, patient data used to assess the patient risk is received at least in part from the medical device.

In a third aspect, a risk-adaptive telemetry system includes: a sensing module, that, when executed by the one or more processors, receives patient data describing a state of a patient who uses a medical device and medical device data describing a state of the medical device; a risk assessment module, that, when executed by the one or more processors, assesses patient risk based at least in part on the patient data that is received, the patient risk reflecting (i) a likelihood that the patient has entered or will enter a patient risk state representative of one or more predetermined physical conditions that do not meet a prescribed level of patient health and (ii) a severity level of the patient risk state, wherein the risk assessment module, when executed by the one or more processors, also assesses medical device risk based at least in part on the medical device data that is received, the medical device risk reflecting (i) a likelihood that the medical device has entered or will enter a medical device risk state indicating that operability of the medical device does not meet a prescribed standard and (ii) a severity level of the device risk state; and a telemetry module, when executed by the one or more processors, selects for transmission to a remote location selected telemetry data associated with the medical device and/or the patient in a manner that is based at least in part on the assessed medical device risk and the assessed patient risk.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. Furthermore, the claimed subject matter is not limited to implementations that solve any or all disadvantages noted in any part of this disclosure.

DETAILED DESCRIPTION

In one aspect, systems and methods are described herein for obtaining telemetry data that is to be transmitted to a remote location, where the telemetry data concerns the state of a system that includes a medical device and a patient or other user of the medical device. As described in more detail below, the particular telemetry data that is obtained and transmitted, as well as the frequency at which it is obtained and transmitted, is determined in part based on an assessment of the system's risk state, including the risk that the patient's health has fallen or will fall below an acceptable level and/or the risk that the operability of the medical device has fallen or will fall below an acceptable level.

The patient risk state may include the patient's past, present and/or predicted future state of health as determined in part by data from the medical device. For instance, if the medical device is a continuous glucose monitor (CGM) that obtains CGM data (blood glucose level data) from the patient, then if the data obtained from the CGM indicates that the patient may enter, e.g., a hypoglycemic state, the amount of telemetry data that is obtained and transmitted to the remote location may be increased. Conversely, if the data obtained from the CGM indicates that the patient is in little or no risk of entering e.g., a hypoglycemic state, the amount of telemetry data that is obtained and transmitted to the remote location may be reduced. Thus, a patient's risk state reflects (i) a likelihood that the patient has entered or will enter a patient risk state representative of one or more predetermined physical conditions (e.g., hypoglycemia) that do not meet a prescribed level of patient health and (ii) a severity level of the patient risk state.

Figure 1:
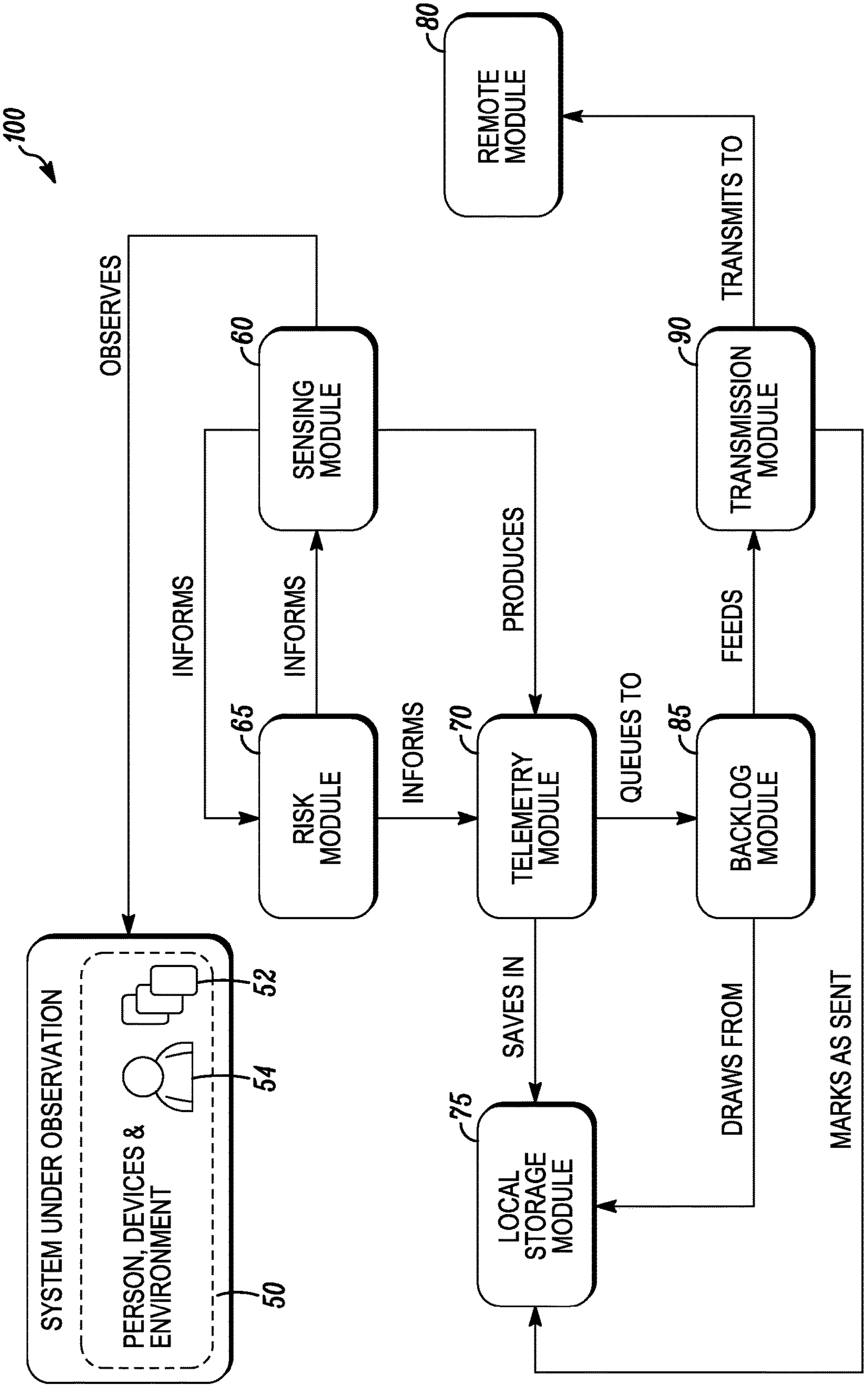
FIG. 1 shows a functional block diagram of one example of a risk-adaptive telemetry system.

FIG. 1 shows a functional block diagram of one example of a risk-adaptive telemetry system 100 that is used to monitor and receive telemetry data from a system 50 being monitored. The monitored system 50 includes one or more devices 52, an individual user 54 of the devices, and the overall environment in which the system operates, The one or more devices 52 in the monitored system 50 generally include one or more medical devices. The medical devices may be devices that monitor the user and/or treat the user in some manner. Illustrative examples of such medical devices may include wearable, embedded, implantable and remote devices including, without limitation, heart monitors, blood glucose monitors, pacemakers, medicant delivery devices (e.g., insulin pumps and pens), implantable defibrillators, neurostimulation devices, and so on.

In addition to the medical device(s), the monitored system 50 may include other devices, some of which may be in communication with the medical device(s). Examples may include communication devices (e.g. smartphones) or other computing devices that receive data from the medical device over a wireless and/or wired network.

may be made of those devices included in the monitored system that include a processor and associated electronics may include, for example, CPU utilization, heap memory allocation, system calls, user-space function invocation count, TCP connection count, link MTU, network latency, queue depth, garbage collection latency, non-volatile storage utilization and/or OS thread count. Of course, a wide variety of other measurements may be made by a wide variety of different sensors depending on the type of system being monitored.

Depending on the sensor type employed, measurements may be analog (e.g., output from am ammeter, voltmeter or galvanometer), or digital. Digital measurements may be scalar, vector, simple or compound values, enumerated constants, strings, integers and real numbers, in various representations. Sensors may be passive or active, continuous or discrete, and may require the cooperation of the elements in the monitored system. In some cases a sensor may even be integrated with the device being monitored (e.g., a call to a logging routine in a software device). Alternatively, some sensors may also operate completely independently of the monitored system (e.g., flying voltage probes applied to a PCB).

By way of example, a software sensor incorporated in an electronic device (e.g., a CGM monitor in this example) may operate as follows:

```
(ns example
  (:require [clojure.tools.logging :as log]))
(if (< egv 54)
    (log/error (Exception. "Severe hypoglycemia") "Patient is below 54 mg/dl"))
```

The example of the risk-adaptive telemetry system 100 shown in FIG. 1 also includes various modules or components that will be discussed in more detail below. As those of ordinary skill in the art will recognize, the features and functions of these various modules may be combined with one another in common modules or components or distributed among different modules in a wide variety of different ways and are not limited to the illustrative example shown in FIG. 1. For instance, it should be noted the sensing module 60, which is used to observe and receive data from the monitored system 50, in some cases may itself in whole or in part be embedded in one or more of the devices 52 included in the monitored system 50. For example, a software device may embed sensing libraries or sub-systems. Conversely, sensing capabilities may be completely external to any of the devices 52. For example, an infrared temperature sensor may provide sensing capability that is external to the monitored system 50.

Each of the various modules of the risk-adaptive telemetry system shown in FIG. 1 will be discussed below.

Sensing Module

The sensing module 60 includes one or more sensors that observe the monitored system, including the medical and other devices, the user and/or the environment. The sensors make measurements of the physical states and/or phenomena of these various elements of the monitored system. Illustrative and non-limiting examples of measurements that may be made, depending on the particular system being monitored, may include humidity, ambient temperature, blood pressure, heart rate, concentrate of ascorbic acid in interstitial fluid, backpressure from a syringe, galvanic skin response and/or battery level. Additional measurements that The sensing module 60 collects measurements of the monitored system 50 from the sensors and provides this information directly or in processed form, in whole or part, to the risk module 65. The sensing module 60 also provides the collected measurements to the telemetry module 70. The sensing module 60 may enhance the collected measurements with annotative metadata, including, for example, the timestamp the measurement was collected, an identification of the sensor used for collection, state information about the sensing module itself, identification of the monitored system, etc. The collected measurements obtained from the sensors may already include information about the importance, severity or timeliness of the observation. However, the sensing module may add or supplement this information with additional severity information and may superimpose another dimension of severity based on accumulated state information.

As explained below, the sensing module provides observations from the sensors as input to the risk module, allowing it to perform risk assessments using measurements of the system under observation.

The sensing module may receive information about the risk state of the monitored system from the risk module. This risk state information may be used as feedback to the sensing module to alter the frequency at which the measurements are made, the particular suite of sensors used for collection of the measurements, the type of observations that are collected, and/or the annotative metadata attached to or otherwise associated with the collected measurements.

Risk Module

The risk module 65 receives data collected by the sensing module and uses it to perform one or more calculations of risk to the system and its individual elements, most especially the user. That is, the risk and sensing modules exist in a feedback loop, with the output from each module being fed to the other as an input. The risk module 65 also feeds forward the risk calculations to the telemetry module 70.

Risk assessment may be performed continuously, at intervals, reactively, and/or on demand. The method(s) of risk assessment may take the form of mathematical models, techniques from the machine learning corpus (e.g. classification algorithms such as logistic regression, support vector machine, naive Bayes classifier, and decision trees), deep learning techniques, etc. Risk calculations may or may not be stateful, taking into account previous states of the monitored system, previous risk states, or historical observations from the sensing module 60.

Telemetry Module

The telemetry module 70 queues high-value telemetry for transmission to the remote module and stores low-value telemetry data in the nonvolatile local storage module. The telemetry module 70 primarily performs a classification function using the risk calculations from the risk module 65. For instance, in low risk states, the telemetry module may send the majority of telemetry data to storage, preserving bandwidth, computing and battery life. On the other hand, as the risks increase, the telemetry module 70 may increase the amount of telemetry data that is sent to the remote module.

Local Storage Module

The local storage module 75 provides nonvolatile storage (i.e., any type of computer memory that can retain information even after power is removed) and/or volatile storage (i.e., computer memory that is subject to loss when power is removed) for telemetry data received from the telemetry module 70. In some embodiments this module may have a "look back" capability. When the risk state is low, the majority of the telemetry data may be stored rather than queued for quick transmission. However, if the risk state increases, it may be useful to provide contextual telemetry from the recent past (prior to the elevated risk) in addition to exigent telemetry data. Conversely, the data in local storage may not be transmitted at all, depending on the system risk state, bandwidth, the severity of the stored data, metadata, etc.

In some embodiments the local storage module 75 may incorporate its own logic for filtering, discarding and classifying received data. It may discard some data outright or choose to place some in volatile storage for quick retrieval, in "hot" nonvolatile storage, or "cold" storage for data unlikely to be needed at all. It may also shuffle data between these classifications and storage mediums over time.

As data in the local storage module 75 are sent to the remote module, they may be marked appropriately by the transmission module. This may provide another opportunity for the local storage module to re-evaluate its choice of storage medium for the data.

Backlog Module

The backlog module 85 pulls telemetry data from the local storage module 75. This may be accomplished using simple mechanisms such as FIFO queues or complex techniques such as structured queries. The backlog module effectively serves as a bridge between the transmission module 90 and the local storage module 75. It draws telemetry data, ostensibly serialized for storage purposes, and reconstitutes it in a form suitable for use by the transmission module 90. As a result, it may supplement the retrieved data elements with additional metadata (such as time of retrieval from storage). If backpressure information is available from the transmission module 90 (e.g., a half- or full-duplex communication channel with receipt acknowledgement such as TCP) the backlog module may adapt its strategy for harvesting telemetry data from the local storage module 75.

Moreover, the combined operation of the local storage module 75, the backlog module 85, the transmission module 90 and the remote module 80 may implement one or more strategies for robust transmission of telemetry data, such as at-least-once delivery, at-most-once delivery, ordering, etc.

Transmission Module

The transmission module 90 serves as the interface to the outside world and the remote module. The transmission module 90 manages (at least) a one-way, linear process in which it encodes a message whose content is one or more elements of telemetry data, and sends it through a communication channel to one or more receivers which decode it. This channel may be simplex, half-duplex, duplex, multicast or broadcast, Channels capable of transmitting and receiving (e.g., half-duplex, duplex, etc) can be used to enhance the operation of the transmission module by enabling receipt of transmission and thus an indication of receiver backpressure, network latency, etc. Acknowledgement of transmitted data also enables telemetry data in the local storage module to be marked as sent.

Remote Module

The remote module 80 functions as a receiver of the telemetry data sent through one or more channels from the transmission module 90. In some embodiments the remote module 80 will not only deserialize the transmissions, but also acknowledge their receipt back to the sender, enabling calculation of backpressure, network latency, etc. Depending on the complexity and sophistication of the remote module 80, the telemetry data received by the remote module 80 may be made available for review and analysis by personnel in a manual process and/or automatically analyzed to generate reports, warnings and so on. The remote module may also be used to reprogram, update operating parameters, send commands or instructions, or otherwise modify the operation of the medical device, which in some cases may occur as a result of the telemetry data that is received.

Figure 3:
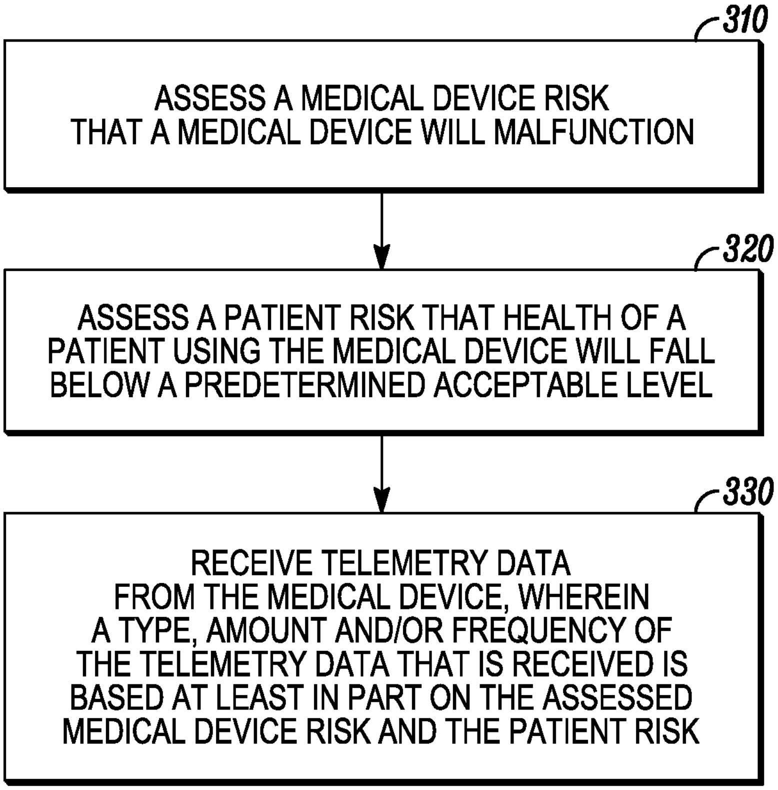
FIG. 3 is a flowchart illustrating one example of a method of communicating telemetry data in a risk-adaptive manner.

As noted above, the features and functions of these various modules may be combined with one another in common modules or distributed among different modules in a wide variety of different ways and are not limited to the illustrative example shown in FIG. 1. For instance, in some embodiments the modules may be implemented using a variety of computing devices such as smartphones, desktop computers, laptop computers, and tablets that include a processor for executing one or more telemetry applications for performing the functionality of various aspects of the risk-adaptive telemetry system described herein and for controlling how the application(s) interact with the sensors, services, or other resources associated with the telemetry system. An example of a suitable computing device is illustrated in FIG. 3.

Illustrative Example

Figure 2:
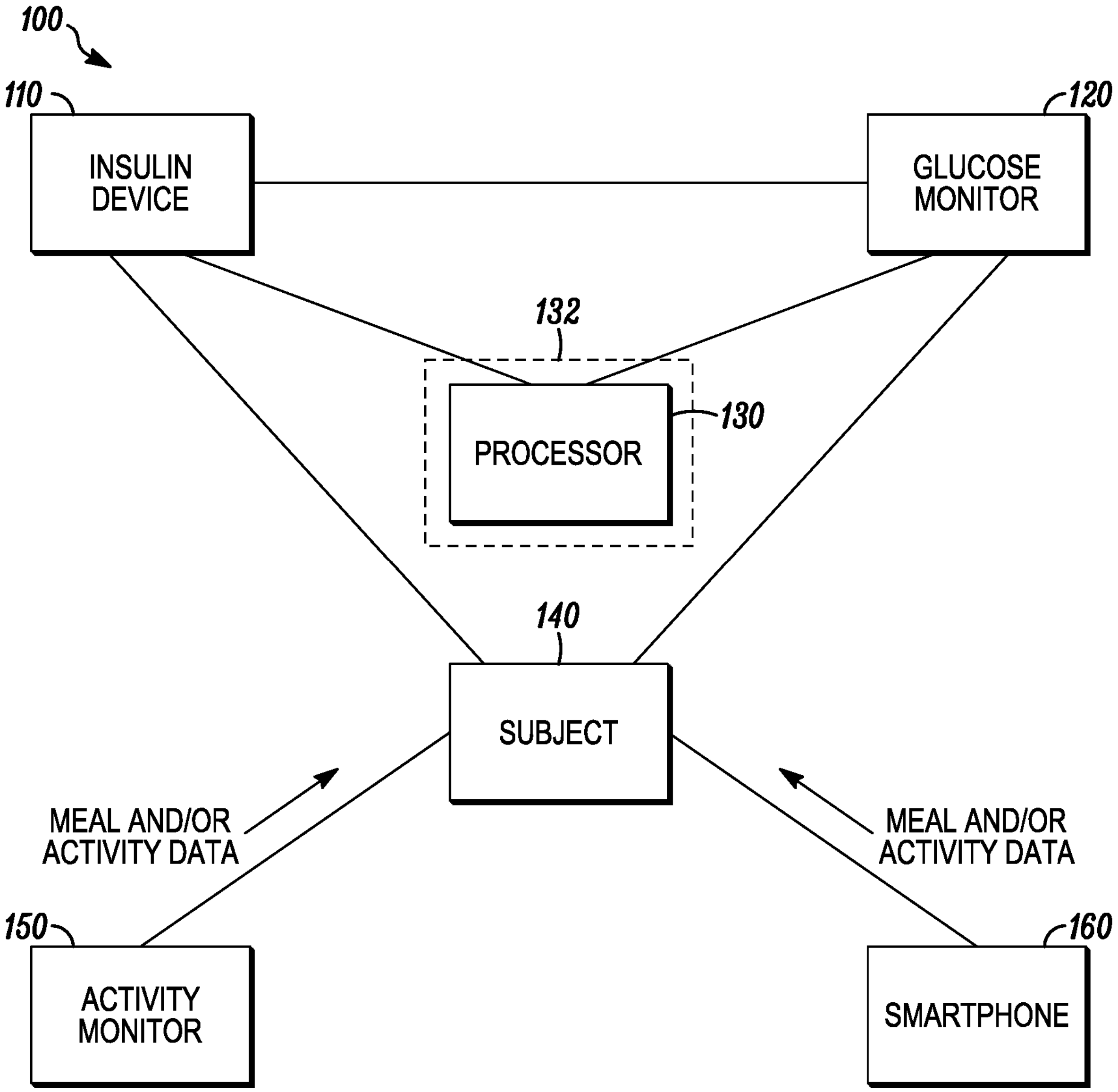
FIG. 2 is a high-level functional block diagram of one example of a monitored system.

FIG. 2 is a high-level functional block diagram of one example of a monitored system 100 (e.g., monitored system 50 in FIG. 1) that may be monitored using the risk-adaptive telemetry system described herein. The monitored system 100 in this example includes two medical devices (e.g., insulin device 110 and glucose monitor 120), a human subject (e.g., subject 140) who is being treated and monitored by the medical devices, and a series of other devices (activity monitor 150, smartphone 160).

The processor 130 communicates with the insulin device 110 and the glucose monitor 120. The insulin device 110 and the glucose monitor 120 communicate with the subject 140 to deliver insulin to the subject 140 and monitor glucose levels of the subject 140, respectively. The processor 130 is configured to perform the calculations described further herein. The insulin device 110 and the glucose monitor 120 may be implemented as separate devices or as a single device, within a single device, or across multiple devices. The processor 130 can be implemented locally in the insulin device 110, the glucose monitor 120, or as standalone device shown dashed lines as standalone device 132 (or in any combination of two or more of the insulin device 110, the glucose monitor 120, or a standalone device). The processor 130 or a portion of the monitored system 100 can be located remotely such as within a server or a cloud-based system.

Examples of insulin devices, such as the insulin device 110, include insulin syringes, external pumps, and patch pumps that deliver insulin to a subject, typically into the subcutaneous tissue. Insulin devices 110 also includes devices that deliver insulin by different means, such as insulin inhalers, insulin jet injectors, intravenous infusion pumps, and implantable insulin pumps. In some embodiments, a subject will use two or more insulin delivery devices in combination, for example injecting long-acting insulin with a syringe and using inhaled insulin before meals. In other embodiments, these devices can deliver other drugs that help control glucose levels such as glucagon, pramlintide, or glucose-like peptide-1 (GLP 1).

Examples of a glucose monitor, such as the glucose monitor 120, include continuous glucose monitors that record glucose values at regular intervals, e.g., 1, 5, or 10 minutes, etc. These continuous glucose monitors can use, for example, electrochemical or optical sensors that are inserted transcutaneously, wholly implanted, or measure tissue non-invasively. Examples of a glucose monitor, such as the glucose monitor 120, also include devices that draw blood or other fluids periodically to measure glucose, such as intravenous blood glucose monitors, microperfusion sampling, or periodic finger sticks. In some embodiments, the glucose readings are provided in near real-time. In other embodiments, the glucose reading determined by the glucose monitor can be stored on the glucose monitor itself for subsequent retrieval.

The insulin device 110, the glucose monitor 120, and the standalone device 132 may be implemented using a variety of computing devices such as smartphones, desktop computers, laptop computers, and tablets. These computing devices may or may not also be used to implement one or more of the modules described above in connection with the risk-adaptive telemetry system 100.

The insulin device 110, the glucose monitor 120, and the standalone device 132 may be in communication through a communications network. The network may be a variety of network types including the public switched telephone network (PSTN), a cellular telephone network, and a packet switched network (e.g., the Internet). This communication network may be the same network in whole or in part over which the transmission module 90 communicates with the remote module 80 to provide the telemetry data. Alternatively, the communications network over which the processor 130 communicates with the various devices in the monitored system 100 may be different from the communication network over which the processor 130 communicates with the various devices in the monitored system 100.

Although only one insulin device 110, one glucose monitor 120, and one processor 130 (within one standalone device 132) are shown in FIG. 1, there is no limit to the number of insulin devices, glucose monitors, processors, and stand-alone devices that may be supported. An activity monitor 150 and/or a smartphone 160 may also be used to collect meal and/or activity data from or pertaining to the subject 140, and provide the meal and/or activity data to the processor 130.

The processor 130 may execute an operating system and one or more applications. The operating system may control which applications are executed by the insulin device 110, the glucose monitor 120, and the standalone device 132, as well as control how the applications interact with one or more sensors, services, or other resources of the insulin device 110, the glucose monitor 120, and the standalone device 132. In some cases the processor 130 may also be used to implement at least some of the functionality of the various modules of the risk-adaptive telemetry system 100 discussed above. For instance, in some embodiments in which at least some of the modules of the telemetry system 100 are implemented using a processor incorporated in a device such as a smartphone, computer or tablet, that same device may be used to implement at least some of the functionality of the monitored system shown in FIG. 2.

FIG. 3 is a flowchart illustrating one example of a method of communicating telemetry data in a risk-adaptive manner. At block 310 a medical device risk that a medical device will malfunction is determined or otherwise assessed. Medical data that is used to assess the risk may be obtained from the medical device and/or other sources. At block 320 a patient risk that the health of a patient using the medical device will fall below a predetermined acceptable level is determined or otherwise assessed. Patient data that is used to assess the risk may be obtained from any suitable source or sources such as the medical device or even self-reported information obtained directly from the patent. At block 330 telemetry data is received from the medical device, where the type, amount and/or frequency of the telemetry data that is received is based at least in part on the assessed medical device risk and the patient risk. In some cases the telemetry data that is received may in whole or in part by transmitted to a remote location for analysis. Likewise, some or all of the telemetry data may be locally stored.

Illustrative Computing Environment

Figure 4:
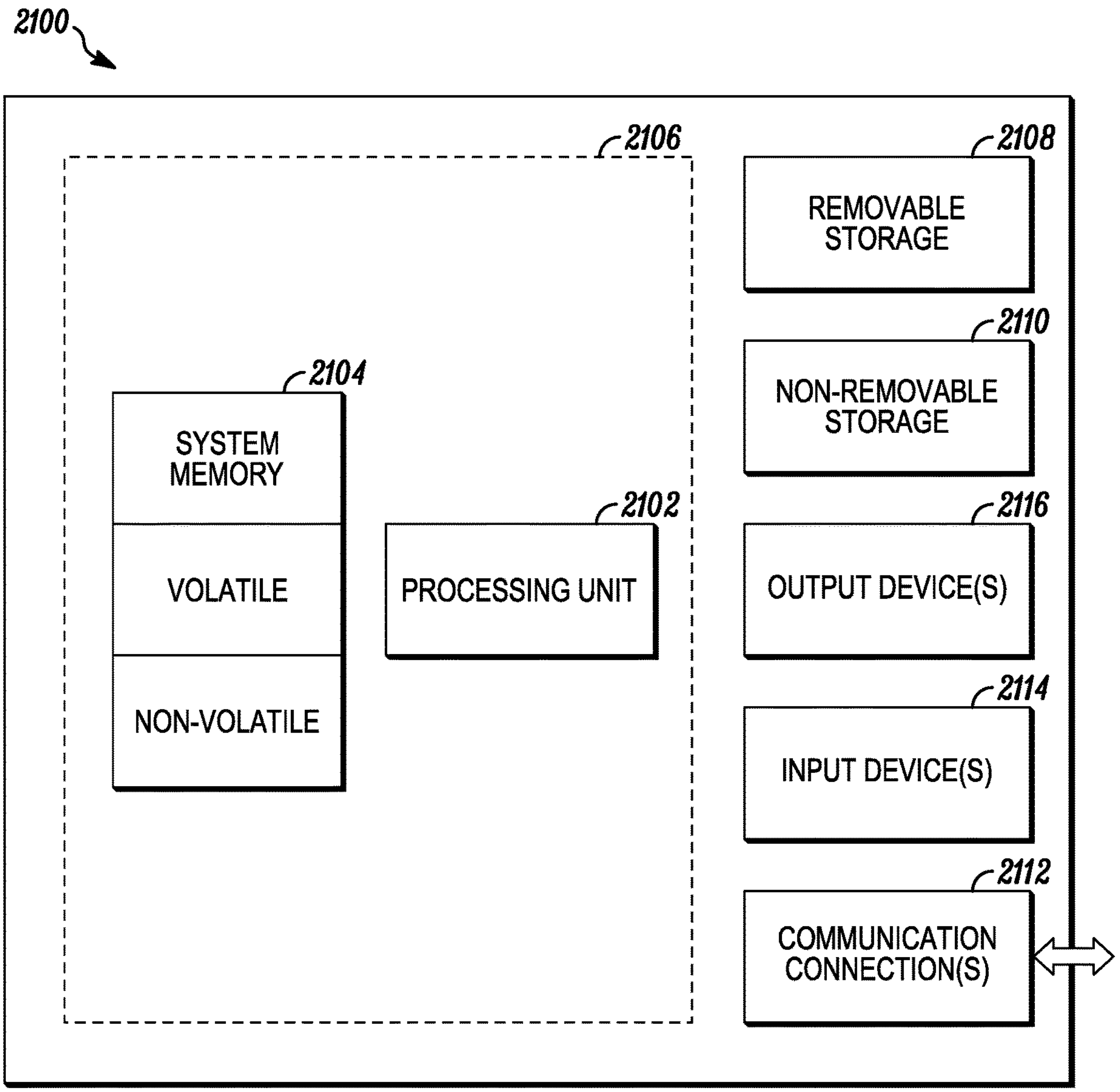
FIG. 4 shows an example of a computing device on which some or all of the functions of the risk-adaptive telemetry system may be performed.

FIG. 4 shows an illustrative computing environment in which example embodiments and aspects may be implemented. For instance, the computing device shown in FIG. 3 may be used to implement the various features and functions of the telemetry system described herein and/or the device or devices that are being monitored by the telemetry system. The computing device environment is only one example of a suitable computing environment and is not intended to suggest any limitation as to the scope of use or functionality.

Numerous other general purpose or special purpose computing devices environments or configurations may be used. Examples of well-known computing devices, environments, and/or configurations that may be suitable for use include, but are not limited to, personal computers, server computers, handheld or laptop devices, multiprocessor systems, microprocessor-based systems, network personal computers (PCs), minicomputers, mainframe computers, embedded systems, distributed computing environments that include any of the above systems or devices, and the like.

Computer-executable instructions, such as program modules, being executed by a computer may be used. Generally, program modules include routines, programs, objects, components, data structures, etc. that perform particular tasks or implement particular abstract data types. Distributed computing environments may be used where tasks are performed by remote processing devices that are linked through a communications network or other data transmission medium. In a distributed computing environment, program modules and other data may be located in both local and remote computer storage media including memory storage devices.

With reference to FIG. 4, an illustrative system for implementing aspects described herein includes a computing device, such as computing device 2100. In its most basic configuration, computing device 2100 typically includes at least one processing unit 2102 and memory 2104. Depending on the exact configuration and type of computing device, memory 2104 may be volatile (such as random access memory (RAM)), non-volatile (such as read-only memory (ROM), flash memory, etc.), or some combination of the two. This most basic configuration is illustrated in FIG. 21 by dashed line 2106.

Computing device 2100 may have additional features/functionality. For example, computing device 2100 may include additional storage (removable and/or non-removable) including, but not limited to, magnetic or optical disks or tape. Such additional storage is illustrated in FIG. 21 by removable storage 2108 and non-removable storage 2110.

Computing device 2100 typically includes a variety of computer readable media. Computer readable media can be any available media that can be accessed by the device 2100 and includes both volatile and non-volatile media, removable and non-removable media.

Computer storage media include volatile and non-volatile, and removable and non-removable non-transitory computer-readable media implemented in any method or technology for storage of information such as computer readable instructions, data structures, program modules or other data. Memory 2104, removable storage 2108, and non-removable storage 2110 are all examples of computer storage media. Computer storage media include, but are not limited to, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by computing device 2100. Any such computer storage media may be part of computing device 2100.

Computing device 2100 may contain communication connection(s) 2112 that allow the device to communicate with other devices. Computing device 2100 may also have input device(s) 2114 such as a keyboard, mouse, pen, voice input device, touch input device, etc. Output device(s) 2116 such as a display, speakers, printer, etc. may also be included. All these devices are well known in the art and need not be discussed at length here.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

The invention claimed is:

1. A method of determining telemetry data that is to be transmitted to a remote location, comprising:

receiving patient data describing a state of a patient who uses a medical device;

receiving medical device data describing a state of the medical device;

assessing patient risk based at least in part on the patient data that is received, the patient risk reflecting (i) a likelihood that the patient has entered or will enter a patient risk state representative of one or more predetermined physical conditions that do not meet a prescribed level of patient health and (ii) a severity level of the patient risk state;

assessing medical device risk based at least in part on the medical device data that is received, the medical device risk reflecting (i) a likelihood that the medical device has entered or will enter a medical device risk state indicating that operability of the medical device does not meet a prescribed standard and (ii) a severity level of the device risk state; and selecting for transmission to a remote location selected telemetry data associated with the medical device and/or the patient in a manner that is based at least in part on the assessed medical device risk and the assessed patient risk.

2. The method of claim 1, further comprising receiving environmental data describing a state of an environment in which the medical device and/or the patient is located, wherein assessing the medical device risk and the patient risk is further based at least in part on the environmental data.

3. The method of claim 1, further comprising causing an adjustment to an amount, type and/or frequency of receipt of the medical device data that is received based at least in part on the assessed medical device risk and the assessed patient risk.

4. The method of claim 1, further comprising causing an adjustment to an amount, type and/or frequency of receipt of the patient data that is received based at least in part on the assessed medical device risk and the assessed patient risk.

5. The method of claim 3, further comprising causing an adjustment to the amount, type and/or frequency of receipt of the patient data that is received based at least in part on the assessed medical device risk and the assessed patient risk.

6. The method of claim 1, wherein selecting for transmission selected telemetry data in a manner that is based at least in part on the assessed medical device risk and the assessed patient risk includes determining a type of telemetry data that is to be transmitted to the remote location and/or a frequency at which the telemetry data is to be transmitted to the remote location.

7. The method of claim 6, wherein the types of telemetry data that are selected and/or the frequency at which the telemetry data is selected for transmission increases as the assessed medical device risk and/or the assessed patient risk increases.

8. The method of claim 6, wherein the types of telemetry data that are selected and/or the frequency at which the telemetry data is selected for transmission decreases as the assessed medical device risk and/or the assessed patient risk decreases.

9. The method of claim 1, wherein the medical device is a continuous glucose monitor and the patient data includes blood glucose data.

10. The method of claim 1, wherein the medical device is selected from the group including pacemakers, implantable defibrillators, medicant delivery devices and neurostimulation devices.

11. The method of claim 1, further comprising locally storing telemetry data that is not selected for transmission.

12. The method of claim 11, further comprising selecting for transmission to the remote location at least some of the locally stored telemetry data when the assessed medical device risk and/or the assessed patient risk increases.

13. The method of claim 3, wherein different types of medical device data are obtained using different types of sensors.

14. The method of claim 13, wherein at least one of the sensors is embedded with the medical device.

15. The method of claim 13, wherein at least one of the sensors is external to the medical device.

16. The method of claim 1, wherein the patient risk and/or the medical device risk is determined using a state calculation that accounts for previous risk states.

17. The method of claim 1, wherein the patient data is received at least in part from the medical device.

18. A risk-adaptive telemetry system comprising a processor configured to:

receive patient data from a medical device describing a state of a patient;

receive medical device data describing a state of the medical device;

assess patient risk based at least in part on the patient data that is received, the patient risk reflecting (i) a likelihood that the patient has entered or will enter a patient risk state representative of one or more predetermined physical conditions that do not meet a prescribed level of patient health and (ii) a severity level of the patient risk state;

assess medical device risk based at least in part on the medical device data that is received, the medical device risk reflecting (i) a likelihood that the medical device has entered or will enter a device risk state indicating that operability of the medical device does not meet a prescribed standard and (ii) a severity level of the device risk state; and select for transmission to a remote location telemetry data associated with the medical device and/or the patient in a manner that is based at least in part on the assessed medical device risk and the assessed patient risk.

19. The risk-adaptive telemetry system of claim 18, wherein the processor is further configured to receive environmental data describing a state of an environment in which the medical device and/or the patient is located, wherein assessing the medical device risk and the patient risk is further based at least in part on the environmental data.

20. The risk-adaptive telemetry system of claim 18, wherein the processor is further configured to cause an adjustment to an amount, type and/or frequency of receipt of the medical device data that is received based at least in part on the assessed medical device risk and the assessed patient risk.

21. The risk-adaptive telemetry system of claim 18, wherein the processor is further configured to cause an adjustment to an amount, type and/or frequency of receipt of the patient data that is received based at least in part on the assessed medical device risk and the assessed patient risk.

22. The risk-adaptive telemetry system of claim 20, wherein the processor is further configured to cause an adjustment to the amount, type and/or frequency of receipt of the patient data that is received based at least in part on the assessed medical device risk and the assessed patient risk.

23. The risk-adaptive telemetry system of claim 18, wherein selecting for transmission selected telemetry data in a manner that is based at least in part on the assessed medical device risk and the assessed patient risk includes determining a type of telemetry data that is to be transmitted to the remote location and/or a frequency at which the telemetry data is to be transmitted to the remote location.

24. The risk-adaptive telemetry system of claim 23, wherein the types of telemetry data that are selected and/or the frequency at which the telemetry data is selected for transmission increases as the assessed medical device risk and/or the assessed patient risk increases.

25. The risk-adaptive telemetry system of claim 23, wherein the types of telemetry data that are selected and/or the frequency at which the telemetry data is selected for transmission decreases as the assessed medical device risk and/or the assessed patient risk decreases.

26. The risk-adaptive telemetry system of claim 18, wherein the medical device is a continuous glucose monitor and the patient data includes blood glucose data.

27. The risk-adaptive telemetry system of claim 18, wherein the medical device is selected from the group including pacemakers, implantable defibrillators, medicant delivery devices and neurostimulation devices.

28. The risk-adaptive telemetry system of claim 18, wherein the processor is further configured to locally store telemetry data that is not selected for transmission.

29. The risk-adaptive telemetry system of claim 28, wherein the processor is further configured to select for transmission to the remote location at least some of the locally stored telemetry data when the assessed medical device risk and/or the assessed patient risk increases.

30. The risk-adaptive telemetry system of claim 20, wherein different types of medical device data are obtained using different types of sensors.

31. The risk-adaptive telemetry system of claim 30, wherein at least one of the sensors is embedded with the medical device.

32. The risk-adaptive telemetry system of claim 30, wherein at least one of the sensors is external to the medical device.

33. The risk-adaptive telemetry system of claim 18, wherein the patient risk and/or the medical device risk is determined using a state calculation that accounts for previous risk states.

34. The risk-adaptive telemetry system of claim 18, wherein the patient data is received at least in part from the medical device.

35. A method of communicating telemetry data, comprising:

assessing a medical device risk that a medical device will malfunction;

assessing a patient risk that health of a patient using the medical device will fall below a predetermined acceptable level; and receiving telemetry data from the medical device, wherein at least one of a type, amount or frequency of the telemetry data that is received and a type, amount, or frequency of telemetry data that is selected for transmission to a remote location is based at least in part on the assessed medical device risk and the patient risk;

selecting for transmission to the remote location at least a portion of the telemetry data that is received;

locally storing telemetry data that is not selected for transmission; and selecting for transmission to the remote location at least some of the locally stored telemetry data when the assessed medical device risk and/or the assessed patient risk increases from a previous risk state.

36. The method of claim 35, wherein the patient risk state is determined at least in part on data received from the medical device.

37. The method of claim 35, further comprising assessing an additional risk state of at least one computing device employed in the assessing and/or receiving and wherein receiving telemetry data from the medical device includes receiving an amount and/or frequency of the telemetry data based at least in part on the assessed additional risk state.

38. The method of claim 35, further comprising receiving environmental data describing a state of an environment in which the medical device and/or the patient is located, wherein assessing the medical device risk and the patient risk is further based at least in part on the environmental data.

39. The method of claim 35, further comprising receiving medical device data describing a state of the medical device and causing an adjustment to an amount, type and/or frequency of the medical device data that is received based at least in part on the assessed medical device risk and/or the assessed patient risk.

40. The method of claim 35, further comprising receiving patient data describing a state of the patent and causing an adjustment to an amount, type and/or frequency of the patient data that is received based at least in part on the assessed medical device risk and/or the assessed patient risk.

41. The method of claim 38, further comprising causing an adjustment to the amount, type and/or frequency of receipt of the patient data that is received based at least in part on the assessed medical device risk and/or the assessed patient risk.

42. The method of claim 35, wherein the types of telemetry data that are selected and/or the frequency at which the telemetry data is selected for transmission increases as the assessed medical device risk and/or the assessed patient risk increases.

43. The method of 35, wherein the types of telemetry data that are selected and/or the frequency at which the telemetry data is selected for transmission decreases as the assessed medical device risk and/or the assessed patient risk decreases.

44. The method of claim 35, wherein the medical device is a continuous glucose monitor and the patient data includes blood glucose data.

45. The method of claim 35, wherein the medical device is selected from the group including pacemakers, implantable defibrillators, medicant delivery devices and neurostimulation devices.

46. The method of claim 35, further comprising selecting for transmission to a remote location at least a portion of the telemetry data that is received and locally storing telemetry data that is not selected for transmission in a nonvolatile local storage module.

47. The method of claim 46, further comprising selecting for transmission to the remote location at least some of the locally stored telemetry data when the assessed medical device risk and/or the assessed patient risk increases, wherein the locally stored telemetry data comprises contextual telemetry from the recent past prior to an elevated risk.

48. The method of claim 39, wherein different types of medical device data are obtained using different types of sensors.

49. The method of claim 48, wherein at least one of the sensors is embedded with the medical device.

50. The method of claim 48, wherein at least one of the sensors is external to the medical device.

51. The method of claim 35, wherein the patient risk and/or the medical device risk is determined using a state calculation that accounts for previous risk states.

52. The method of claim 35, wherein patient data used to assess the patient risk is received at least in part from the medical device.

53. A risk-adaptive telemetry system, comprising:

a sensing module, that, when executed by the one or more processors, receives patient data describing a state of a patient who uses a medical device and medical device data describing a state of the medical device;

a risk assessment module, that, when executed by the one or more processors, assesses patient risk based at least in part on the patient data that is received, the patient risk reflecting (i) a likelihood that the patient has entered or will enter a patient risk state representative of one or more predetermined physical conditions that do not meet a prescribed level of patient health and (ii) a severity level of the patient risk state, wherein the risk assessment module, when executed by the one or more processors, also assesses medical device risk based at least in part on the medical device data that is received, the medical device risk reflecting (i) a likelihood that the medical device has entered or will enter a medical device risk state indicating that operability of the medical device does not meet a prescribed standard and (ii) a severity level of the device risk state; and a telemetry module, when executed by the one or more processors, selects for transmission to a remote location selected telemetry data associated with the medical device and/or the patient in a manner that is based at least in part on the assessed medical device risk and the assessed patient risk.

* * * * *